US006190307B1

(12) United States Patent
Tsai

(10) Patent No.: US 6,190,307 B1
(45) Date of Patent: Feb. 20, 2001

(54) AUXILIARY EROTIC IMPLEMENT

(76) Inventor: Chi-Wen Tsai, No. 486, Chung-Cheng Road., Shu-Lin Town, Taipei Hsien (TW)

( * ) Notice: Under 35 U.S.C. 154(b), the term of this patent shall be extended for 0 days.

(21) Appl. No.: 09/302,455

(22) Filed: Apr. 30, 1999

(51) Int. Cl.[7] .................................. A61F 5/00; A61H 1/00

(52) U.S. Cl. .................................. 600/38; 601/46; 601/51; 601/84

(58) Field of Search .................................. 600/38; 601/46, 601/50, 51, 52, 53, 54, 69, 84, 97, 138

(56) References Cited

U.S. PATENT DOCUMENTS 3,991,751 * 11/1976 O'Rourke .................................. 600/38
4,790,296 * 12/1988 Segal .................................. 600/38
5,470,303 * 11/1995 Leonard et al. .......................... 600/38

* cited by examiner

*Primary Examiner*—John P. Lacyk
(74) *Attorney, Agent, or Firm*—Dougherty & Troxell

(57) ABSTRACT

An auxiliary erotic implement includes a body, a vibrator, a transmitting unit, and an changeover switch. the body has an intermediate portion provided with a layer of rolling beads under the surface, and the vibrator provided on an outer surface of a rear portion. the transmitting unit is container in the body, consisting of a motor, tow gear and rod sets, a slide plate, an interacting gear and an interacting rod. The body is rotated for 360° and move axially back and forth at the same time by the two gear and rod sets rotated by the motor controlled by the changeover switch and cooperated by the interacting gear, the interacting rod and the slide plate. In addition, the rolling beads also roll together with the body, enhancing worth of the implement and pleasure to be acquired.

2 Claims, 5 Drawing Sheets

AUXILIARY EROTIC IMPLEMENT

BACKGROUND OF THE INVENTION

This invention relates to an auxiliary erotic implement, particularly to one having multiple uses for enhancing pleasure in life.

A conventional auxiliary erotic implement generally includes a body of a male organ shape with low protruding lines on its surface, and a transmitting unit rotating the body so as to obtain pleasure. But its movement is monotonous and is limited in its effect.

SUMMARY OF THE INVENTION

A main objective of the invention is to offer an auxiliary erotic implement having a transmitting unit provided with a transmitting shaft with a curved end permitting a body to rotate for 360° and to move axially back and forth as well, acquiring multiple changes in its movement.

Another objective of the invention is to offer an auxiliary erotic implement having a layer of plural rolling beads provided under the surface of the intermediate portion of the body and rolling with the body when the body is rotated by the transmitting unit.

The feature of the invention is a body, a vibrator, a transmitting unit, and a changeover switch. Plural rolling beads are provided under the surface of the intermediate portion of the body. The transmitting unit is contained in the body, with the changeover switch affixed on an outer surface of a rear portion. The motor of the transmitting unit supplies force for rotating the body for 360° and the body moving back and forth at the same time in a preset period of time, with rolling beads rolling together with the body, enhancing its worth and pleasure.

BRIEF DESCRIPTION OF DRAWINGS

This invention will be better understood by referring to the accompanying drawings, wherein.

DETAILED DESCRIPTION OF THE PREFERRED EMBODIMENT

Figure 1:
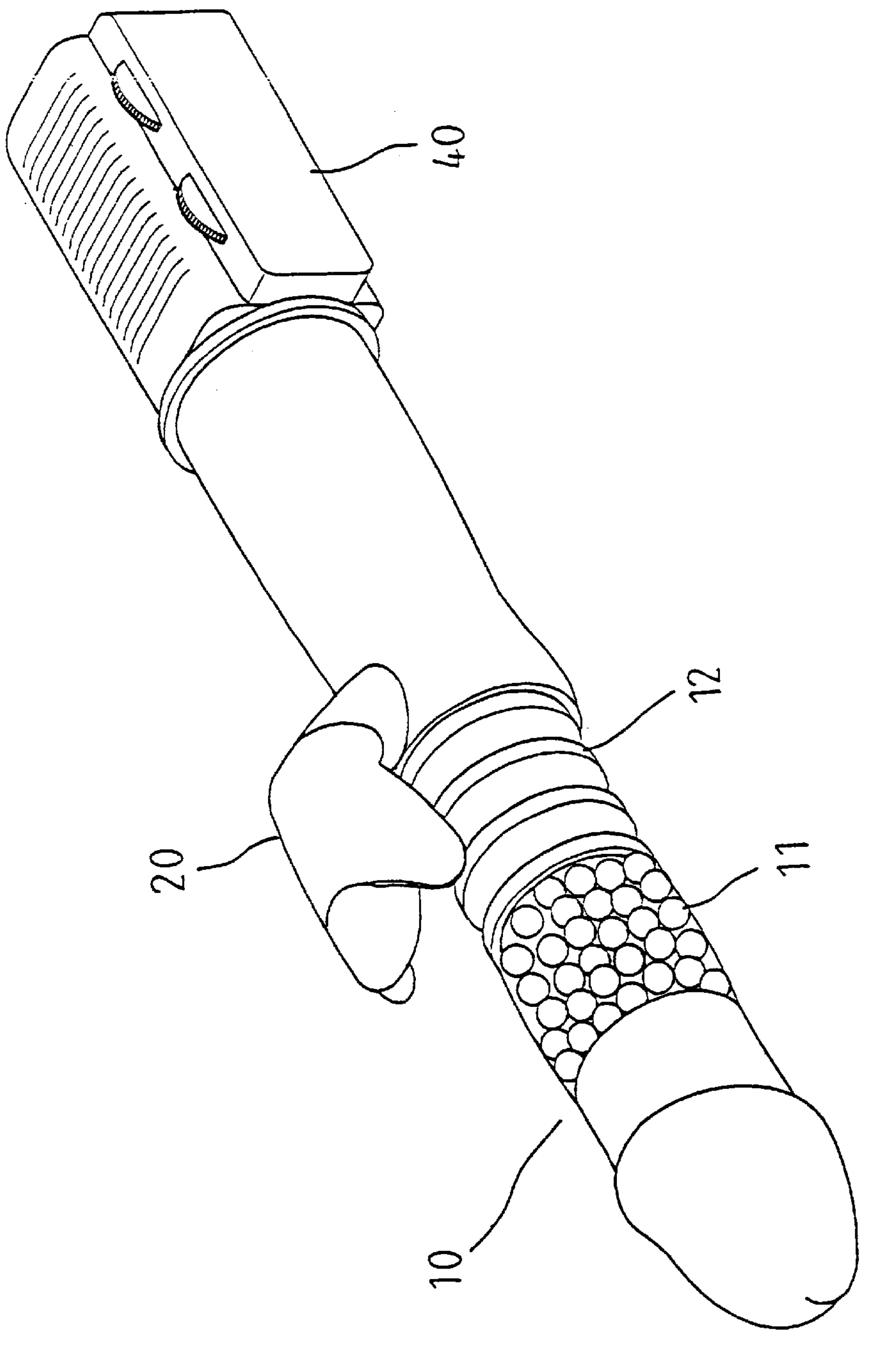
FIG. 1 is a perspective view of an auxiliary erotic implement in the present invention.
Figure 2:
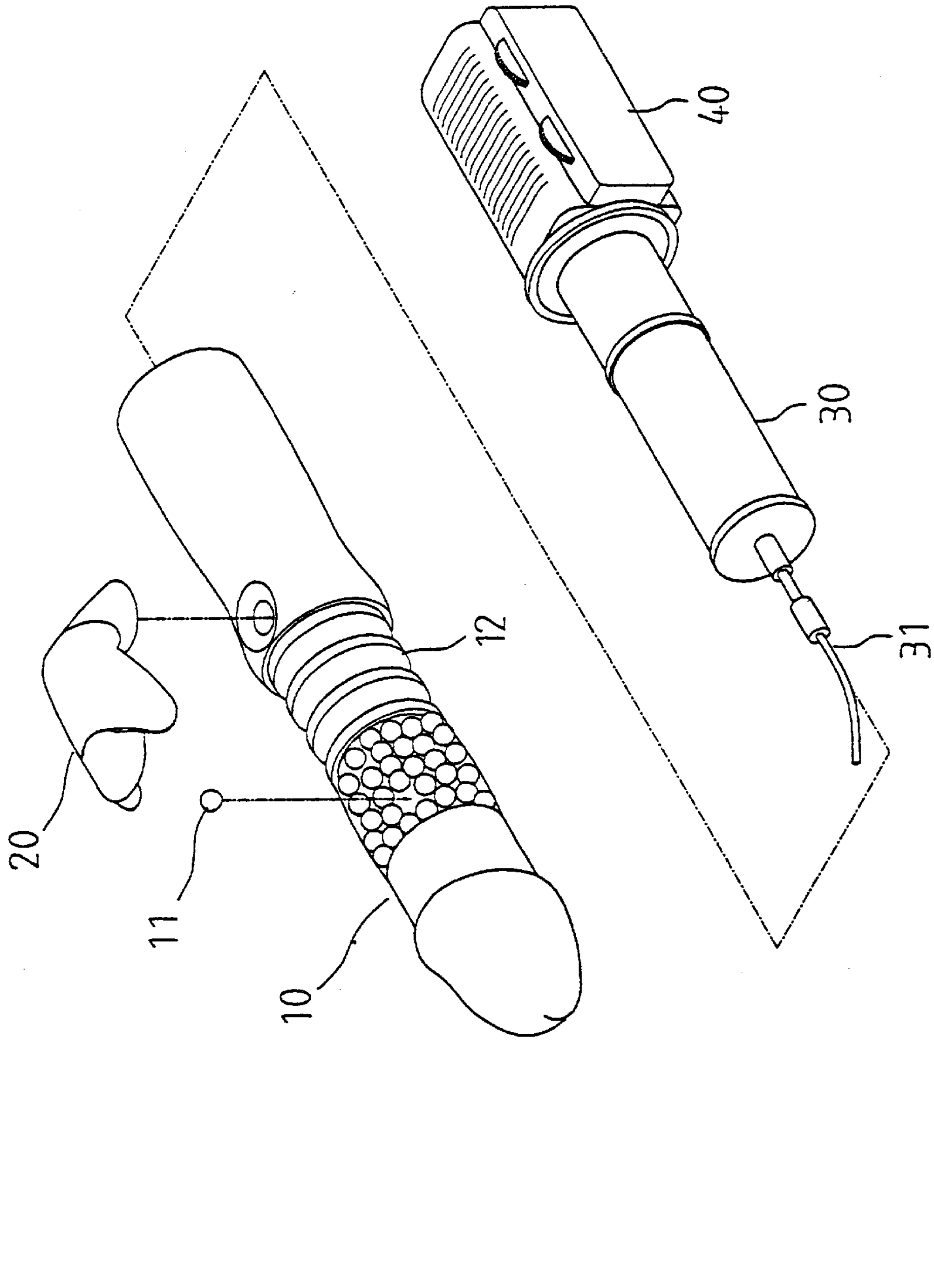
FIG. 2 is an exploded perspective view of the auxiliary erotic implement in the present invention.

A preferred embodiment of an auxiliary erotic implement in the present invention, as shown in FIGS. 1 and 2, includes a body 10, a vibrator 20, a transmitting unit 30, and a changeover switch 40 as main components combined together.

The body 10 has a shape like a male organ, and an intermediate portion with a layer of rolling beads 11 arranged regularly under the surface, rotated by a transmitting shaft 31 of the transmitting unit 30. A rings-shaped elastic member 12 is formed in a rear portion abutting the rolling beads 11, permitting the body 10 have enough space to move back and forth.

The vibrator 20 is placed on an outer surface of the body 10 and located behind the elastic member 12, controlled in its movement by the changeover switch 40.

Figure 3:
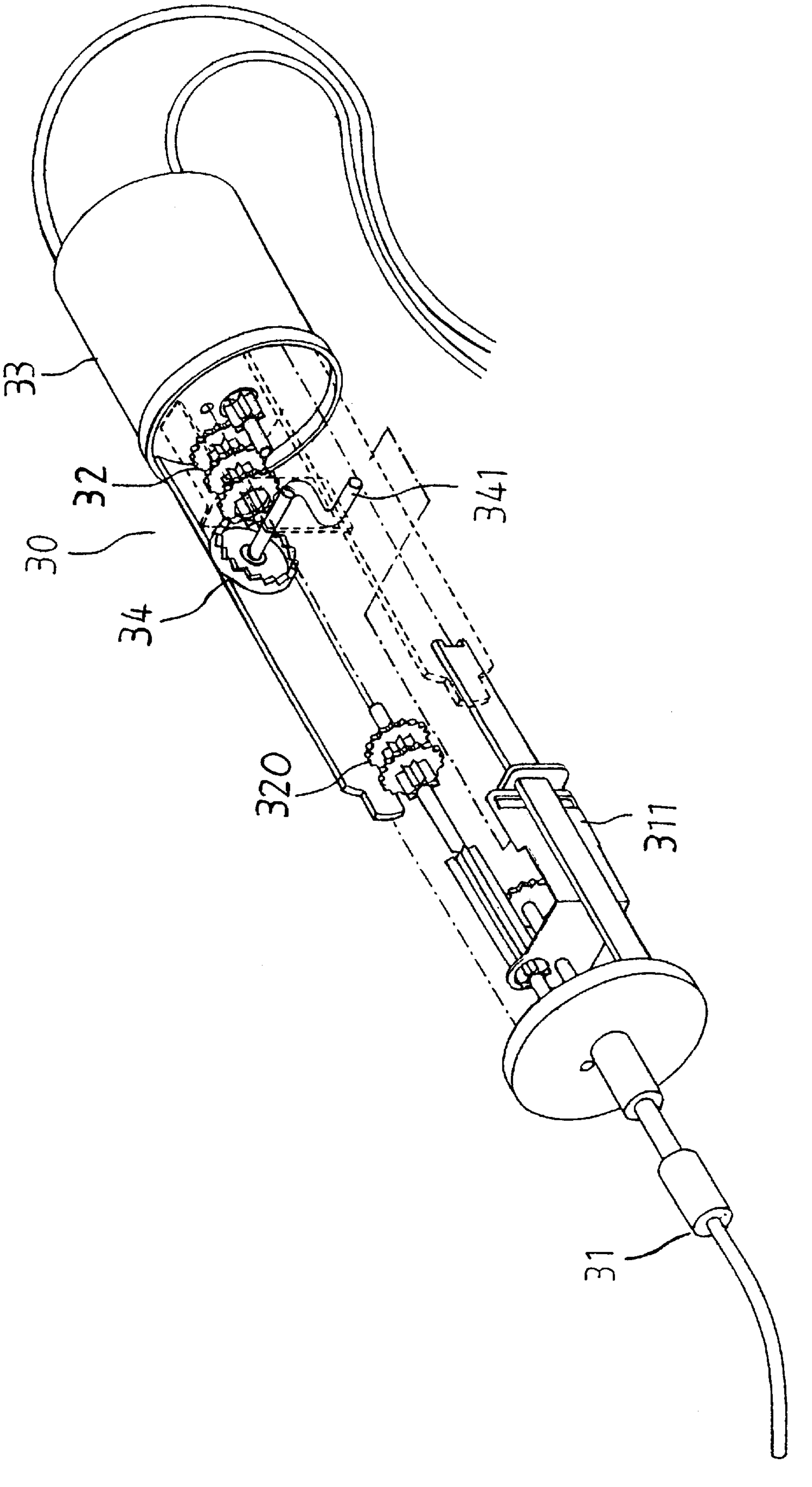
FIG. 3 is an exploded perspective view of the transmitting unit in the present invention.
Figure 4:
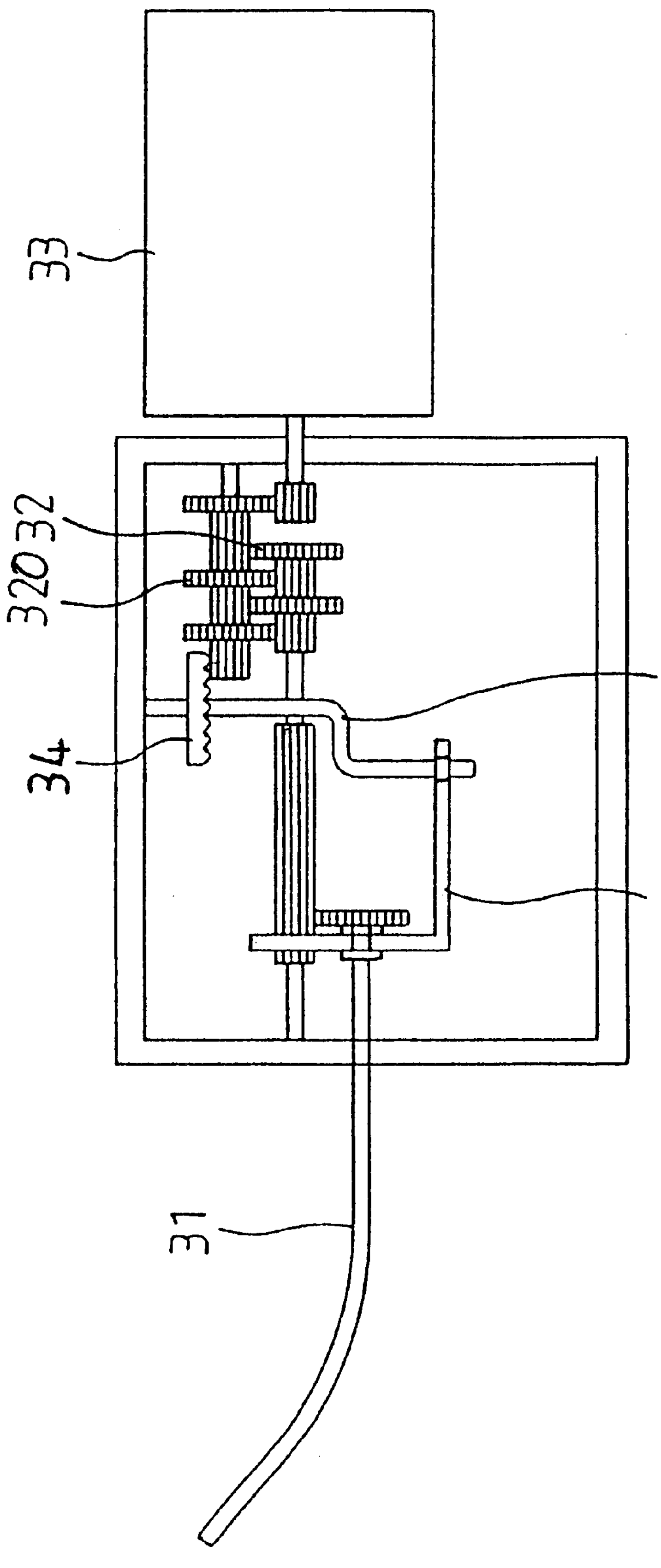
FIG. 4 is an upper view of the transmitting unit in the present invention; and, FIG. 5 is a perspective view of the movement of the auxiliary erotic implement in the present invention.
Figure 5:
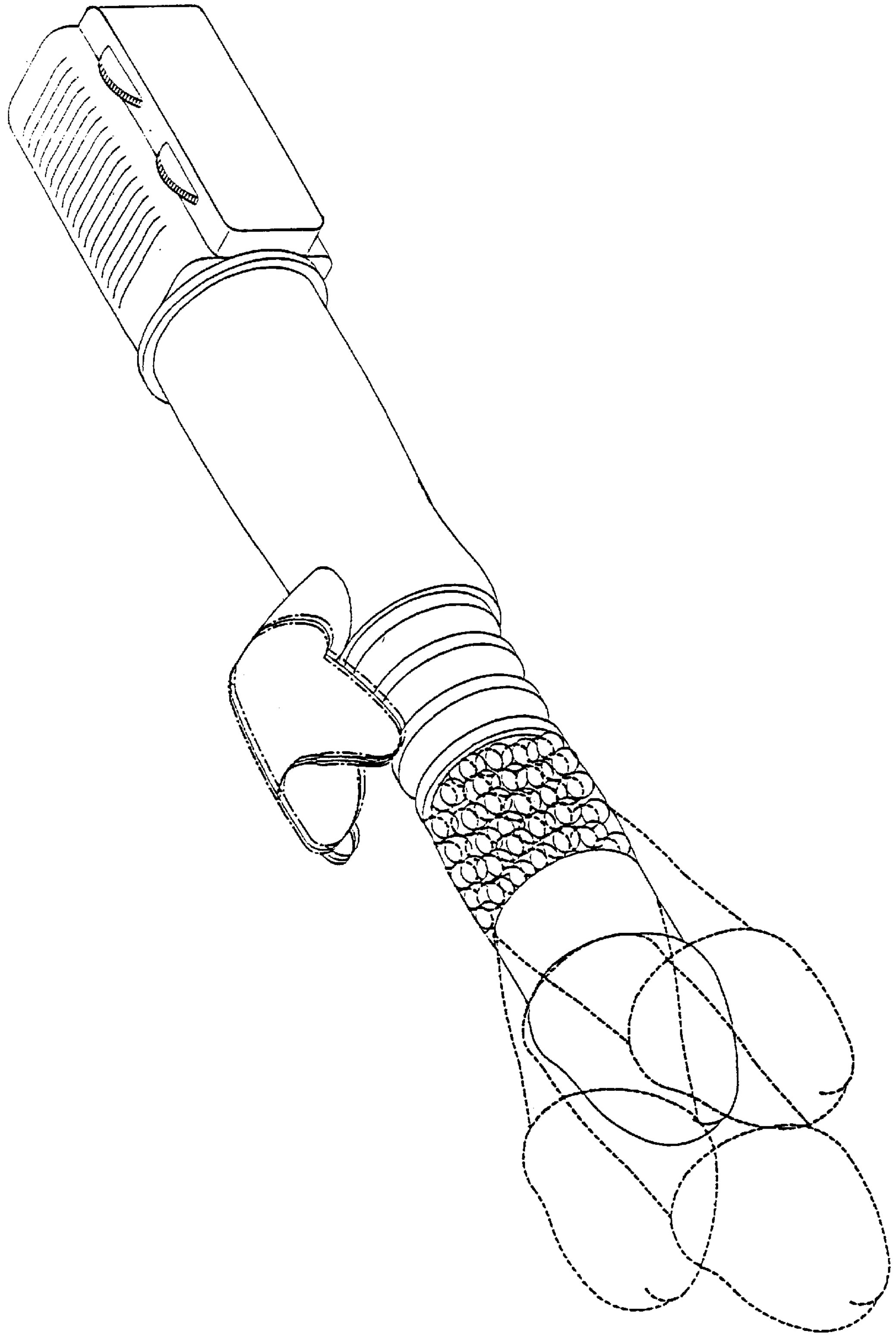

The transmitting unit 30, as shown in FIGS. 3 and 4, consists of the transmitting shaft 31, two gear and rod sets 32, 320, a motor 33, an interacting gear 34, and an interacting rod 341. The motor 33 supplies force to the gear and rod sets 32, 320, and the first gear and rod set 32 engages the transmitting shaft 31 having its front portion curved and rotated by the motor 33 so that the body 10 may be rotated for 360° and wit hits outer end swaying around inclinedly for a little angle from the axis, with the rolling beads 11 rolling at the same time. Then the second gear and rod set 320 engages the interacting gear 34, with the interacting rod 341 functioning as a shaft of the interacting gear 34 with a bent middle and connected with a slide plate 311 at its end. Then the interacting rod 341 is rotated by the interacting gear 34 to cause the slide plate 311 move back and forth, when the motor 33 rotates.

The changeover switch assembly 40 is affixed on an outer surface of the rear end portion of the body 10, operated to turn on and off the body 10 and the vibrator 20.

Next, as shown in FIGS. 3 and 4, when the auxiliary erotic implement is to be used, a first (the right one) of the changeover switch assembly 40 is turned on to start the motor 33 to let the vibrator 20 vibrate, and a second (the left one) of the switch assembly 40 is turned on to let the body 10 rotate and move back and forth. In addition, the rolling beads 11 also roll together with the body 10, so various movements are performed to increase pleasure.

While the preferred embodiment of the invention has been described above, it will be recognized and understood that various modifications may be made therein and the appended claims are intended to cover all such modifications which may fall within the spirit and scope of the invention.

What is claimed is:

1. An auxiliary erotic implement comprising:

a body having a front and a rear portion, the front portion having first and second ends, the first end being shaped like a male organ, an intermediate portion between the first and second ends being provided with a layer of rolling beads and a rings-shaped elastic member at the second end;

a vibrator positioned on an outer surface of the rear portion of said body rearwardly of and adjacent to said rings-shaped elastic member;

a transmitting unit located in said body, providing a transmitting force to said body so as to rotate the front portion of the body 360° while moving the front portion back and forth at the same time a preset distance with said rolling beads rolling the same time; and, a changeover switch assembly affixed on an outer surface of the rear portion of said body, and controlling the operation of the vibrator and the transmitting unit.

2. The auxiliary erotic implement as claimed in claim 1, wherein said transmitting unit comprises: a transmitting shaft having a curved outer end; a slide plate connected to the transmitting shaft, first and second gear and rod sets, a motor, an interacting gear, and an interacting rod; said motor rotating at the same time said first and second gear and rod sets, the first gear and rod set connected to and rotating said transmitting shaft with the curved end, the second gear and rod set engaged with and rotating said interacting gear and said interacting rod, said interacting rod connected to said slide plate so as to reciprocate said slide plate and said transmitting shaft whereby said first end of said body is rotated for 360° and moved axially back and forth at the same time.

* * * * *